United States Patent

Tanaka et al.

[11] 4,259,202
[45] Mar. 31, 1981

[54] CLEANING AND PRESERVATIVE SOLUTION FOR CONTACT LENSES

[75] Inventors: Kyoichi Tanaka; Akira Tsuzuki, both of Nagoya, Japan

[73] Assignee: Toyo Contact Lens Co., Ltd., Nagoya, Japan

[21] Appl. No.: 45,053

[22] Filed: Jun. 4, 1979

[30] Foreign Application Priority Data

Feb. 27, 1979 [JP] Japan .................. 54/22662

[51] Int. Cl.$^3$ .................. C11D 1/66; C11D 3/22
[52] U.S. Cl. .................. 252/107; 252/106; 252/108; 252/174.17; 252/174.18; 252/121
[58] Field of Search .................. 252/106, 108, 174.18, 252/DIG. 1, DIG. 14, 107, 121; 134/40, 42; 424/78, 80; 536/119

[56] References Cited

U.S. PATENT DOCUMENTS

| | | | |
|---|---|---|---|
| 2,893,990 | 7/1959 | Hass et al. | 536/119 |
| 2,999,858 | 9/1961 | Curtis | 536/119 |
| 3,141,013 | 7/1964 | O'Boyle | 536/119 X |
| 3,702,364 | 11/1972 | Boghosian et al. | 424/324 |
| 3,872,020 | 3/1975 | Yamagishi et al. | 252/174.18 |
| 3,882,036 | 6/1975 | Krezanoski et al. | 252/106 |
| 3,884,826 | 5/1975 | Phares et al. | 252/106 |
| 3,954,644 | 5/1976 | Krezanoski et al. | 252/106 |
| 4,013,576 | 3/1977 | Loshaek | 252/106 |
| 4,046,706 | 9/1977 | Krezanoski | 252/106 |
| 4,104,187 | 8/1978 | Sibley et al. | 252/106 |
| 4,127,423 | 11/1978 | Rankin | 134/30 |

FOREIGN PATENT DOCUMENTS 51-38290 3/1976 Japan.

Primary Examiner—P. E. Willis, Jr.
Attorney, Agent, or Firm—Armstrong, Nikaido, Marmelstein & Kubovcik

[57] ABSTRACT

A cleaning and preservative solution for contact lenses which contains as an effective ingredient a monoester of saccharose with a fatty acid having the general formula:

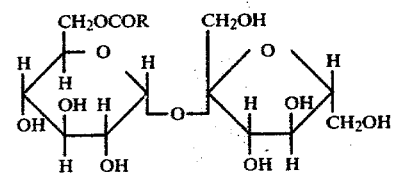

wherein R is a saturated or unsaturated aliphatic hydrocarbon group having 8 to 18 carbon atoms. The solution has excellent cleaning and preservative effects. Contact lenses can be cleaned during the preservation of the lenses with soaking them in the solution.

6 Claims, 2 Drawing Figures

CLEANING AND PRESERVATIVE SOLUTION FOR CONTACT LENSES

BACKGROUND OF THE INVENTION

The present invention relates to a novel cleaning and preservative solution for contact lenses. More particularly, it relates to a solution which can be used for cleaning contact lenses as well as for preserving contact lenses.

Heretofore various kinds of contact lenses have been used. As typical contact lenses there are water-nonabsorptive contact lenses made of polymethyl methacrylate or silicone rubber and water-absorptive contact lenses made of predominantly poly-2-hydroxyethyl methacrylate or polyvinyl pyrrolidone.

Recently there have been also proposed water-nonabsorptive hard contact lenses having an oxygen permeability which are made of materials such as poly-4-methylpentene-1 (see Japanese Patent Publication No. 22320/1972), cellulose acetate butyrate (see U.S. Pat. No. 3,900,250) and a copolymer of (polysiloxanyl)alkyl methacrylate and methyl methacrylate (see Japanese Patent Publication No. 33502/1977).

When those contact lenses, particularly water-nonabsorptive contact lenses are worn on eyes, their surfaces are contaminated mainly by sebum being a secretion in eyes. For this reason, the contact lenses removed from eyes should be cleaned immediately to remove the contamination such as sebum fixed to the surfaces thereof. The wear of insufficiently cleaned contact lenses results in a great cause for uncomfortable symptoms such as foggy sight, pain and ocular injection.

A usual method adopted for cleaning contact lenses is that in which a cleaning solution containing a salt of a polyoxyethylene higher alkyl ether sulfuric acid ester is applied to both surfaces of contact lenses and the surfaces are then rubbed with fingers. The contact lenses cleaned are rinsed with a running water or a physiological saline solution and then stored in a preservative solution containing ingredients such as sodium chloride, a buffer and a bactericide. The storage of the contact lenses in the preservative solution is important, particularly as to the water-absorptive contact lenses, to maintain them in a hydrous state. With the water-nonabsorptive contact lenses, it is also preferable to store them in the preservative solution in order to maintain the surfaces of the lenses in a hydrophilic state, to reduce a foreign body sensation when the lenses are worn on eyes and to store the lenses sanitarily so that they are ready in a clean state for the next wear.

In a conventional use of contact lenses, the cleaning and preservation of contact lenses are carried out separately with using different cleaning and preservative solutions, which requires a considerably troublesome labor.

The conventional use has an another disadvantage that the surfaces of contact lenses are damaged in the cleaning thereof since the lenses are rubbed with fingers. Particularly the oxygen-permeable hard contact lenses tend to be damaged more readily since generally they have a poor surface hardness in comparison with the common hard contact lenses made of polymethyl methacrylate. In case of contact lenses made of a water-repellent or hydrophobic material such as silicone rubber, they are sometimes subjected to a treatment for making the surfaces thereof hydrophilic such as applying a corona discharge to the surfaces of graft-copolymerizing a hydrophilic monomer such as 2-hydroxyethyl methacrylate to the surfaces for the purpose of improving the affinity of the lenses to cornea. When such treated contact lenses are washed by rubbing with fingers, the surfaces made hydrophilic are damaged, which results in the decrease of the lifetime as contact lenses.

In case of cleaning contact lenses by rubbing with fingers, there frequently occurs an unforeseen accident that the lenses slip out of the fingers and are missing.

The cleaning solution for the water-nonabsorptive contact lenses is prepared in many cases with paying no regard to the safety against ocular tissues since the material of the lenses is water-nonabsorptive. Therefore, when the contact lenses which are not rinsed sufficiently after cleaning or in which some ingredients of the cleaning solution still remain after rinse are worn on eyes, an accident that the eyes are irritated occurs. Furthermore, such a serious accident tends to occur that the cleaning solution is used erroneously instead of a wetting agent which is applied to the surfaces of the water-nonabsorptive lenses in wearing thereof in order to improve the hydrophilic property of the surfaces thereof and the ocular tissues are damaged fatally.

When the previously mentioned conventional cleaning solution containing a chemical such as a salt of a polyoxyethylene higher alkyl ether sulfuric acid ester as a main ingredient for water-nonabsorptive contact lenses is used for cleaning the above-mentioned water-nonabsorptive contact lenses of which surfaces are treated to become hydrophilic or water-nonabsorptive contact lenses having a hydrophilic surface as described in the same assignee's U.S. Patent Application Ser. No. 944,843, the main ingredient of the cleaning solution tends to be adsorbed onto the hydrophilic surfaces of the contact lenses. Since the adsorbed ingredient is not removed readily by rinsing the lenses with a running water, the adsorption of the ingredient of the cleaning solution is not suitable from a viewpoint of safety against ocular tissues and further the hydrophilic property of the lens surfaces is sometimes hindered by the adsorbed ingredient, by which the proper functions of contact lenses are influenced badly.

OBJECTS OF THE INVENTION

It is an object of the present invention to provide a novel cleaning and preservative solution for contact lenses which has such excellent cleaning and preservative effects that contaminations such as sebum fixed to the surfaces of the lenses are removed merely by preserving the lenses therein for a desired period.

A further object of the invention is to provide a cleaning and preservative solution which is harmless to ocular tissues.

Another object of the invention is to provide a cleaning and preservative solution of which ingredients are not adsorbed onto the surfaces of water-nonabsorptive contact lenses having a hydrophilic surface so that the ingredients can be readily removed by rinsing with a running water.

These and other objects of the invention will become apparent from the description hereinafter.

DETAILED DESCRIPTION

It has now been found out that the above-mentioned objects can be attained by a cleaning and preservative solution containing as an effective ingredient a monoester of saccharose with a fatty acid having the following general formula:

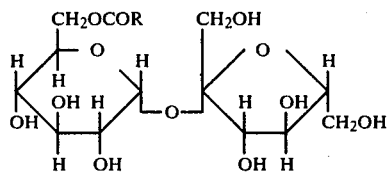

wherein R is a saturated or unsaturated aliphatic hydrocarbon group having 8 to 18 carbon atoms.

The cleaning and preservative solution of the present invention containing the above-mentioned monoester of saccharose has an excellent cleaning effect and an excellent preservative effect, so that contaminations such as sebum fixed to the surfaces of contact lenses can be removed during the preservation of the lenses with soaking them in the solution of the present invention. Furthermore the solution of the present invention is harmless to ocular tissues. In addition, even when the solution of the prevent invention is used for cleaning and preserving water-nonabsorptive contact lenses having a hydrophilic surface, the monoester of saccharose as the effective ingredient of the solution of the present invention is not adsorbed onto the hydrophilic surface of the contact lenses, so that the monoester of saccharose is removed readily by means such as rinsing with a running water.

Figure 1:
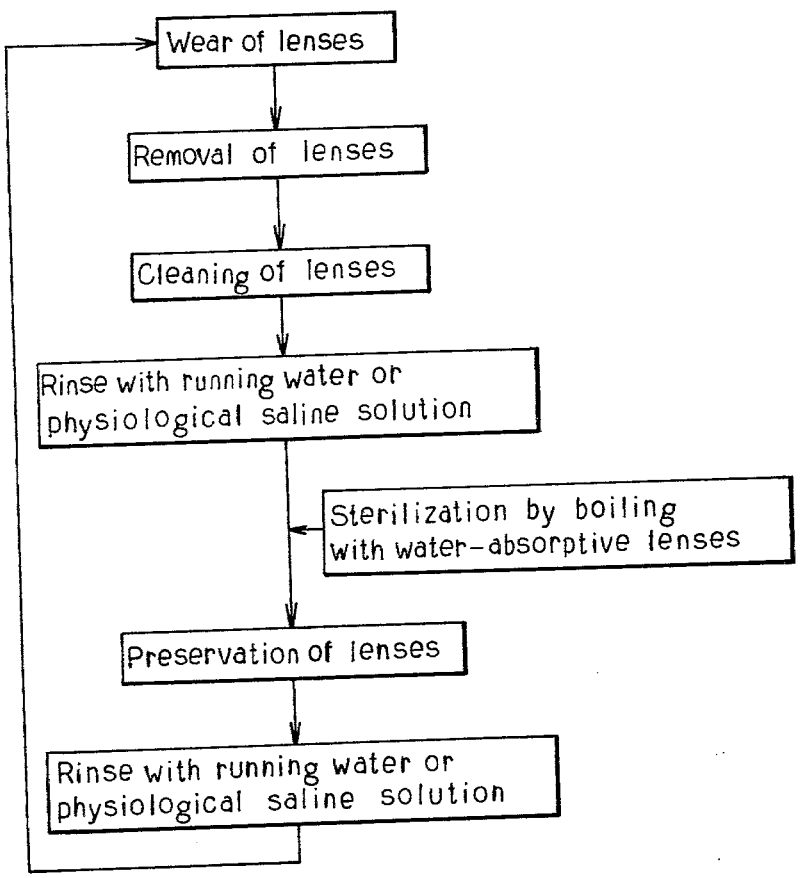
FIG. 1 is a flow chart showing the handlings of contact lenses in order in a conventional use thereof.
Figure 2:
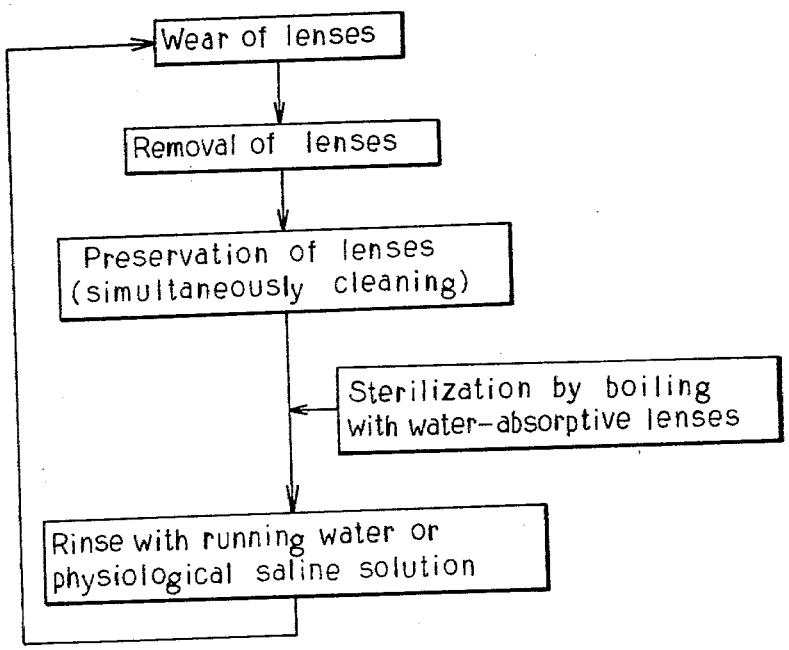
FIG. 2 is a flow chart showing the handlings of contact lenses in order in case of using the cleaning and preservative solution of the present invention.

As mentioned previously, in the conventional manner for handling contact lenses, the cleaning and preservation of contact lenses should be carried out separately with using different cleaning and preservative solutions. The conventional manner for handling contact lenses is shown in FIG. 1. In case of using the cleaning and preservative solution of the present invention, however, the cleaning of contact lenses is effected during the preservation thereof and the troublesome procedure as in the conventional manner is settled, as is clear from FIG. 2 showing a manner for handling contact lenses in case of using the cleaning and preservative solution of the present invention. The contact lenses cleaned and preserved in the solution of the present invention can be worn on eyes after simply rinsing with a running water or a physiological saline solution. Furthermore, in case of using the solution of the present invention, contact lenses are cleaned only by soaking them in the solution and it is unnecessary to wash the lenses by rubbing with fingers as in the conventional manner. Therefore, the damage of the lens surfaces and the miss of the lenses due to the washing by rubbing with fingers are prevented.

The monoester of saccharose employed as an effective ingredient in the present invention is prepared by esterifying a fatty acid having the general formula: RCOOH wherein R is a saturated or unsaturated hydrocarbon group having 8 to 18 carbon atoms, preferably 10 to 14 carbon atoms with saccharose. When the number of the carbon atoms of the group R is less the above range, the cleaning effect of the monoester of saccharose is reduced. When the number of the carbon atoms of the group R is more than the above range, the solubility of the monoester of saccharose to water is decreased.

Examples of the monoester of saccharose employed in the present invention include saccharose monodecylate, saccharose monoundecylate, saccharose monolaurate, saccharose monotridecylate, saccharose monomyristate, saccharose monononanate, saccharose monopentadecylate, saccharose monopalmitate, saccharose monoheptadecylate, saccharose monostearate, saccharose monooleate, saccharose monolinoleate and saccharose monolinolenate. These monoesters of saccharose may be used alone or in combination.

The monoesters of saccharose are commercially available. Generally the monoester of saccharose commercially available contains diester of saccharose or triester of saccharose in addition to one or more monoesters of saccharose. For instance, a monoester of saccharose available under a commercial name "LWA-1540" made by Ryoto Kabushiki Kaisha contains about 40% by weight of saccharose monolaurate as a main component and further contains other monoester and diester such as saccharose monomyristate and saccharose dilaurate. Such a commercially available monoester of saccharose can be suitably used in the present invention, particularly from a view-point of the low costs thereof.

The monoesters of saccharose are widely used as food additives such as emulsifying agent and dispersing agent, and are absolutely harmless to human body.

The present invention has been accomplished on the basis of the present invetors's following findings: The monoester of saccharose is highly safe to ocular tissues. The monoester of saccharose shows an excellent cleaning effect and contact lenses can be cleaned only by soaking them in an aqueous solution of the monoester of saccharose for preservation. Even when the aqueous solution of the monoester of saccharose is used for cleaning and preserving water-nonabsorptive contact lenses having a hydrophilic surface, the monoester of saccharose is not adsorbed onto the surfaces of the lenses.

The cleaning and preservative solution of the present invention is an aqueous solution which contains preferably 0.01 to 0.5 w/v % (hereinafter referred merely to as "%"), more preferably 0.1 to 0.3% of the monoester of saccharose. When the concentration of the monoester is less than the above range, the cleaning effect is reduced. When the concentration of the monoester is less than the above range, the cleaning effect is reduced. When the concentration of the monoester is more than the above range, the cleaning effect corresponding to such a high concentration is not expected.

Preferably the cleaning and preservative solution of the present invention contains further a polysaccharide or its derivative as an auxiliary ingredient in addition to the monoester of saccharose as an effective ingredient for the purposes of still more improving the cleaning effect of the monoester of saccharose and of preventing the contaminations released from contact lenses from fixing again to the lenses.

Examples of the polysaccharide and its derivative include alkali metal salts of alginic acid, alkali metal salts of pectic acid, pectic acid derivatives, dextran, xanthan gum, tragacanth gum, agar, locust bean gum, guar gum, methyl cellulose, alkali metal salts of carboxymethyl cellulose, alkali metal salts of carboxyethyl cellulose, methyl propyl cellulose, hydroxyethyl cellulose, hydroxypropyl cellulose, hydroxypropyl methyl cellulose and alkali metal salts of chondroitin sulfuric acid. Preferable alkali metal salts are sodium salt and potassium salt. These polysaccharides and their derivatives may be used alone or in combination.

The above-mentioned polysaccharides and their derivatives possess at least one property of thickening property, dispersing property and lubricating property and are suitably used as an auxiliary ingredient in the solution of the present invention.

The concentration of the auxiliary ingredient in the solution of the present invention varies depending upon the kind and degree of polymerization of the auxiliary ingredient employed. Usually the concentration of the auxiliary ingredient is from 0.01 to 10%. When the concentration of the auxiliary ingredient is less than the above range, the thickening, dispersing and lubricating effects are not sufficiently exhibited. When the concentration of the auxiliary ingredient is more than the above range, the effect corresponding to such a high concentration is not expected.

The cleaning and preservative solution of the present invention may contain further conventional agents such as buffer, bactericide and chelating agent in addition to the monoester of saccharose and the polysaccharide or its derivative as the auxiliary ingredient.

Examples of the buffer employed in the present invention include ophthalmology-physiologically acceptable buffers such as combinations of boric acid and its sodium salt, phosphoric acid and its sodium salt, citric acid and its sodium salt, lactic acid and its sodium salt, amino acid (such as glycine or glutamic acid) and its sodium salt, and malic acid and its sodium salt. The buffer is used at a concentration of about 0.01 to about 1 mole/liter, preferably about 0.03 to about 0.15 mole/liter. The buffer prevents the hydrolysis of the monoester of saccharose as the effective ingredient to stabilize the solution of the present invention. The buffer also maintains the solution of the present invention at a pH value of 4.8 to 8.5, preferably 7 to 7.4 which is near the pH value of tears, so that the contour of contact lenses are stabilized. The stabilization of the lens contour is important particularly as to water-absorptive contact lenses.

The bactericide is used for preventing the propagation of bacteria during the preservation of contact leness in the solution of the present invention so that the contact lenses are not contaminated by bacteria. Examples of the bactericide used in the present invention include ophthalmology-physiologically acceptable bactericides such as thimerosal, chlorohexizine, phenylmercuric nitrate, benzalkonium chloride and chlorobutanol. The concentration of the bactericide in the solution of the present invention varies depending upon the kind of the bactericide employed. Usually the bactericide is used at a concentration of 0.0001 to 0.5%.

The chelating agent is used for preventing a metal ion such as calcium ion from fixing to the surfaces of contact lenses and for removing the metal ion fixed to the surfaces of contact lenses. The preferable Example of the chelating agent employed is sodium ethylenediaminetetraacetate.

When a compound liberating an alkali metal ion in an aqueous solution, for instance, sodium alginate being one of the polysaccharides mentioned above or sodium phosphate being one of the buffers mentioned above, is added to an aqueous solution of the monoester of saccharose, the clouding point of the aqueous solution of the monoester of saccharose which is usually not less than 100° C. is lowered rapidly and the aqueous solution becomes turbid with being tinged with milk white even at a temperature below a normal temperature. As a result, the cleaning and preservation of contact lenses are disturbed. In the present invention, it has been found out that such a problem is settled by adding a desired amount of an alkali metal salt of a saturated fatty acid to the aqueous solution of the monoester of saccharose. That is to say, by the addition of such an alkali metal salt, the clouding point of the aqueous solution of the monoester of saccharose is maintained not less than 100° C. to give a clear aqueous solution at a normal temperature. The addition of the alkali metal salt has an another advantage that the hydrolysis of the monoester of saccharose is depressed.

As the alkali metal salt of the fatty acid, there are exemplified alkali metal salts of saturated fatty acid having an alkyl group of 7 to 18 carbon atoms, including sodium salts and potassium salts of capric acid, lauric acid, myristic acid, palmitic acid and stearic acid. The alkali metal salt is usually employed at a concentration of 0.001 to 1%, preferably 0.005 to 0.03%.

The cleaning and preservative solution of the present invention is prepared by dissolving the monoester of saccharose and in case of need, one or more ingredients mentioned above into water, preferably a distilled water.

The present invention is more particularly described and explained by means of the following Examples.

EXAMPLES 1 to 10

Ten kinds of aqueous solutions were prepared by dissolving the ingredients shown in Table 1 into a distilled water. The proportions of the ingredients in Table 1 are shown by % (w/v %) in the aqueous solution.

TABLE 1

| Ingredient | Example No. | | | | | | | | | |
|---|---|---|---|---|---|---|---|---|---|---|
| | 1 | 2 | 3 | 4 | 5 | 6 | 7 | 8 | 9 | 10 |
| Saccharose monomyristate | 0.2 | 0.2 | — | — | — | — | — | — | — | — |
| P-1570 | — | — | 0.2 | 0.2 | — | — | — | — | — | — |
| S-1570 | — | — | — | — | 0.2 | — | — | — | — | — |
| LWA-1540 | — | — | — | — | — | 0.2 | 0.2 | 0.3 | 0.4 | — |
| OWA-1570 | — | — | — | — | — | — | — | — | — | 0.2 |
| Sodium alginate | — | 0.2 | — | 0.2 | 0.2 | 0.1 | 0.2 | 0.2 | 0.2 | 0.2 |
| Sodium carboxymethyl cellulose | — | 0.1 | — | 0.1 | 0.1 | — | 0.3 | 0.1 | 0.1 | — |
| Sodium chondroitin sulfate | — | — | — | — | — | 0.1 | — | — | — | — |
| Glycine | — | 1.0 | — | 1.0 | 1.0 | 1.0 | — | 1.0 | 1.0 | 1.0 |
| Boric acid | — | — | — | — | — | — | 2.0 | — | — | — |

TABLE 1-continued

| Ingredient | Example No. | | | | | | | | | |
|---|---|---|---|---|---|---|---|---|---|---|
| | 1 | 2 | 3 | 4 | 5 | 6 | 7 | 8 | 9 | 10 |
| Sodium hydroxide | — | 0.0016 | — | 0.0016 | 0.0016 | 0.0016 | 0.156 | 0.0016 | 0.0016 | 0.0016 |
| Thimerosal | — | 0.001 | — | 0.001 | 0.001 | 0.001 | 0.001 | 0.001 | 0.001 | 0.001 |
| Sodium laurate | — | 0.0111 | — | 0.0111 | 0.0111 | — | 0.0111 | 0.0167 | 0.002 | — |
| Sodium myristate | — | — | — | — | — | 0.0123 | — | — | — | 0.0123 |

Note
P-1570: Commercial name of a monoester of saccharose containing saccharose monopalmitate as a main component, made by Ryoto Kabushiki Kaisha.
S-1570: Commercial name of a monoester of saccharose containing saccharose monostearate as a main component, made by Ryoto Kabushiki Kaisha.
LWA-1540: Commercial name of a monoester of saccharose containing saccharose monolaurate as a main component, made by Ryoto Kabushiki Kaisha.
OWA-1570: Commercial name of a monoester of saccharose containing saccharose monooleate as a main component, made by Ryoto Kabushiki Kaisha.

The cleaning and preservative solutions obtained were subjected to the following tests.

(1) Test for determining cleaning effect

An artificial sebum consisting of the following components was prepared.

| Component | Part by weight |
|---|---|
| Tripalmitin | 1.50 |
| Cetanol | 0.50 |
| Palmitic acid | 1.00 |
| Oleic acid | 1.00 |
| Linolic acid | 1.00 |
| Spermaceti (note) | 1.50 |
| Cholesterol | 0.50 |
| Cholesterol palmitate | 0.50 |
| Lecithin | 0.75 |

Note:
Commercial name of a higher alcohol ester of higher fatty acid containing cetyl myristate as a main component, made by Nippon Oil and Fats Co., Ltd.

The obtained artificial sebum was applied uniformly to commercially available water-nonabsorptive contact lenses cleaned sufficiently by means of ultrasonic washing. As the contact lens, a water-nonabsorptive contact lens having a hydrophilic surface produced according to the process described in U.S. Patent Application Ser. No. 944,843, available under a commercial name "MENICON $O_2$" made by Toyo Contact Lens Co., Ltd. was used. The contact lenses were then dried in vacuo to fix the artificial sebum to the surfaces thereof.

Two ml. portions of each aqueous solution obtained in Examples 1 to 10 were added into 10 preservative containers for contact lens, respectively. The contaminated contact lenses were placed into the containers with one lens per one container and allowed to stand for 6 hours.

For the purpose of comparison, 2 ml. portions of a commercially available cleaning solution for water-nonabsorptive contact lens containing a sodium salt of a polyoxyethylene alkyl ether sulfuric acid ester as a main ingredient (available under a commercial name "HARD CLEAN" made by Toyo Contact Lens Co., Ltd.) were added into 10 preservative containers, respectively. The contaminated contact lenses were placed into the containers with one lens per one container and allowed to stand for 6 hours.

After soaking for 6 hours, the contact lenses were taken out from the containers, rinsed with a running water for 10 seconds and dried in vacuo.

With the thus cleaned contact lenses, the haze (%) was determined by using a hazeometer according to the method provided in JIS K 6714. Preliminarily, the haze (%) was determined with the contact lenses before the contaminating treatment in the same manner. The hazes of the contact lenses before the contaminating treatment ranged from 0.3 to 0.5%. The value obtained by subtracting the haze of the contact lens before the contaminating treatment from the haze of the cleaned contact lens is shown in Table 2. The cleaning effect is better as the value in Table 2 is smaller.

TABLE 2

| Lens No. | Example No. | | | | | | | | | | Conventional cleaning solution |
|---|---|---|---|---|---|---|---|---|---|---|---|
| | 1 | 2 | 3 | 4 | 5 | 6 | 7 | 8 | 9 | 10 | |
| 1 | 0.07 | 0.10 | 0.15 | 0.07 | 0.12 | 0.14 | 0.10 | 0.19 | 0.08 | 0.25 | 0.08 |
| 2 | 0.13 | 0.06 | 0.05 | 0.10 | 0.08 | 0.12 | 0.15 | 0.14 | 0.06 | 0.15 | 0.40 |
| 3 | 0.15 | 0.05 | 0.35 | 0.08 | 0.07 | 0.15 | 0.18 | 0.12 | 0.12 | 0.08 | 0.30 |
| 4 | 0.13 | 0.10 | 0.12 | 0.06 | 0.18 | 0.15 | 0.12 | 0.04 | 0.09 | 0.07 | 0.75 |
| 5 | 0.18 | 0.08 | 0.08 | 0.15 | 0.12 | 0.20 | 0.15 | 0.13 | 0.06 | 0.22 | 0.72 |
| 6 | 0.09 | 0.13 | 0.20 | 0.06 | 0.15 | 0.16 | 0.12 | 0.15 | 0.09 | 0.14 | 0.43 |
| 7 | 0.17 | 0.08 | 0.10 | 0.12 | 0.20 | 0.15 | 0.10 | 0.06 | 0.08 | 0.13 | 0.79 |
| 8 | 0.15 | 0.06 | 0.15 | 0.10 | 0.18 | 0.10 | 0.08 | 0.18 | 0.14 | 0.08 | 0.55 |
| 9 | 0.10 | 0.15 | 0.07 | 0.35 | 0.11 | 0.13 | 0.16 | 0.05 | 0.13 | 0.09 | 0.37 |
| 10 | 0.14 | 0.12 | 0.16 | 0.15 | 0.25 | 0.20 | 0.10 | 0.14 | 0.15 | 0.19 | 0.42 |
| Average | 0.13 | 0.09 | 0.14 | 0.12 | 0.15 | 0.15 | 0.13 | 0.12 | 0.10 | 0.14 | 0.55 |

(2) Test for determining influence on the hydrophilic property of contact lens

The same contact lenses as used in Test (1) were subjected to the following test after sufficiently cleaned by means of ultrasonic washing.

Two ml. portions of each aqueous solution obtained in Examples 1 to 10 or the commercially available cleaning solution "HARD CLEAN" were added into 10 preservative containers, respectively, in the same manner as described above. The cleaned contact lenses were placed into the containers with one contact lens per one container and allowed to stand for 6 hours.

After soaking for 6 hours, each contact lens was taken out from the container and rinsed with a running water for 10 seconds. Immediately the surface of the contact lens was observed with naked eye to determine whether the surface of the contact lens was covered with water. All contact lenses preserved in each aqueous solution obtained in Examples 1 to 10 were covered with water, which fact shows that the contact lenses maintained the original excellent hydrophilic property. On the other hand, in case of the contact lenses preserved in the conventional cleaning solution, 8 pieces out of 10 pieces repelled water on the whole surface or a part thereof.

(3) Test for determining toxicity

Into one eye of five male albino rabbits was dropped 0.1 ml. of each aqueous solution obtained in Examples 1 to 10. The other eye for blank was untreated.

After 0.5 hour from the dropping, the response of the ocular tissue of each rabbit was observed. No abnormal phenomenon was observed in the ocular tissues of all rabbits and there was no substantial distinction between the treated eye and the blank eye.

The above tests reveals the following facts: The cleaning and preservative solution of the present invention has an excellent cleaning effect. Contact lenses can be cleaned only by soaking them in the solution of the present invention. Even when the solution of the present invention is used for cleaning and preserving water-nonabsorptive contact lenses having a hydrophilic surface, the solution does not have a bad influence on the hydophilic property of the lenses since the ingredients of the solution can be readily removed by rinsing. Furthermore, the solution of the present invention is harmless to ocular tissues.

The cleaning and preservative solution of the present invention is suitably used for cleaning and preserving water-absorptive contact lenses as well as water-nonabsorptive contact lenses without any trouble and problem encountered in handling contact lenses with using the conventional cleaning solution and the preservative solution.

What is claimed is:

1. A cleaning and preservative solution for contact lenses comprised of: as an effective ingredient a monoester of saccharose in a concentration of 0.01 to 0.5 w/v %, a compound selected from the group consisting of a polysaccharide and a polysaccharide derivative, in a concentration of 0.01 to 10 w/v %: said monoester being a saccharose fatty ester having the following general formula:

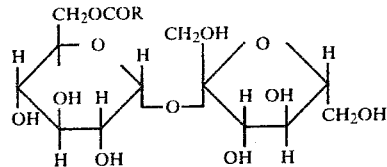

wherein R is a saturated or unsaturated aliphatic hydrocarbon group having 8 to 18 carbon atoms; and an alkali metal salt of a saturated fatty acid in a concentration of 0.001 to 1 w/v % having an alkyl group of 7 to 18 carbon atoms.

2. The cleaning and preservative solution of claim 1, in which the monoester of saccharose is at least one member selected from the group consisting of saccharose monodecylate, saccharose monoundecylate, saccharose monolaurate, saccharose monotridecylate, saccharose monomyristate, saccharose monononanate, saccharose monopentadecylate, saccharose monopalmitate, saccharose monoheptadecylate, saccharose monostearate, saccharose monooleate, saccharose monolinoleate amd saccharose monolinolenate.

3. The cleaning and preservative solution of claim 1, in which the polysaccharide or its derivative is at least one member selected from the group consisting of alkali metal salt of alginic acid, alkali metal salt of pectic acid, pectic acid derivative, dextran, xanthan gum, tragacanth gum, agar, locust bean gum, guar gum, methyl cellulose, alkali metal salt of carboxymethyl cellulose, alkali metal salt of carboxyethyl cellulose, methyl propyl cellulose, hydroxyethyl cellulose, hydroxypropyl cellulose, hydroxypropyl methyl cellulose and alkali metal salt of chondroitin sulfuric acid.

4. The cleaning and preservative solution of claim 1, which further contains an ophthalmology-physiologically acceptable buffer in a concentration of about 0.01 to about 1 mole/liter.

5. The cleaning and preservative solution of claim 1, which further contains an ophthalmology-physiologically acceptable bactericide in a concentration of 0.0001 to 0.5 w/v %.

6. The cleaning and preservative solution of claim 1, which further contains an ophthalmology-physiologically acceptable buffer in a concentration of about 0.01 to 1 mole/liter and an ophthalmology-physiologically acceptable bactericide in a concentration of 0.0001 to 0.5 w/v %.

* * * * *